US005773416A

United States Patent [19]
Chehab

[11] Patent Number: 5,773,416
[45] Date of Patent: Jun. 30, 1998

[54] METHODS FOR RESTORING OR ENHANCING REPRODUCTIVE FUNCTION IN REPRODUCTIVELY IMPAIRED HOSTS

[75] Inventor: Farid F. Chehab, San Francisco, Calif.

[73] Assignee: The Regents of the University of California, Oakland, Calif.

[21] Appl. No.: 735,038

[22] Filed: Oct. 22, 1996

Related U.S. Application Data

[60] Provisional application No. 60/006,106 Oct. 25, 1995.

[51] Int. Cl.$^6$ ............................................. A61K 38/00
[52] U.S. Cl. ............................................. 514/21
[58] Field of Search ............................................. 514/21

[56] References Cited

FOREIGN PATENT DOCUMENTS

WO 96/29405   9/1996   WIPO .

OTHER PUBLICATIONS

Chehab, F. et al., "A broader role for leptin," *Nature Medicine*, 2(7) :723–724 (1996).
Barash, I.A. et al., "Leptin is a Metabolic Signal to the Reproductive System," *Endocrinology* 137(7):3144–3147 (1996).
Campfield, L.A. et al., "Recombinant Mouse OB Protein: Evidence for a Peripheral Signal Linking Adiposity and Central Neural Networks," *Science* 269:546–549 (1995).
Chehab, F. et al., "Correction of the sterility defect in homozygous obese female mice by treatment with the human recombinant leptin," *Nature Genetics* 12:318–320 (1996).
Coleman, D.L., et al., "Effects of parabiosis of normal with genetically diabetic mice," *Am. J. Physiology* 217(5):1298–1304 (1969).
Coleman, D.L., "Effects of Parabiosis of Obese with Diabetes and Normal Mice," *Diabetologia* 9:294–298 (1973).
Drasher, M.L. et al., "Physiological Differences in Uteri of Obese Stock Mice," *J. Heredity* 46(6):209–212 (1955).
Frederich, R.C. et al., "Leptin levels reflect body lipid content in mice: Evidence for diet induced resistance to leptin action," *Nature Medicine* 1(12):1311–1314 (1995).
Frisch, R.E. et al., "Height and Weight at Menarche and a Hypothesis of Critical Body Weights and Adolescent Events," *Science* 169:397–399 (1970).
Frisch, R.E. et al., "Menstrual Cycles: Fatness as a Determinant of minimum Weight for Height Necessary for Their Maintenance or Onset," *Science* 185:949–951 (1974).
Frisch, R.E. et al., "Delayed Menarche and Amenorrhea in Ballet Dancers," *N. Eng. J. Med.* 303(1):17–19 (1980).
Frisch, R.E. et al., "Delayed Menarche and Amenorrhea of College Athletes in Relation to Age of Onset of Training," *J. Am. Med. Assoc.* 246(14):1559–1563 (1981).
Progress in Reproductive Biology and Medicine: Adipose Tissue and Reproduction Frisch, R.E. ed., Karger, Basel, Switzerland, vol. 14 (1990).

Halaas, J.L. et al., "Weight–Reducing Effects of the Plasma Protein Encoded by the obese Gene" *Science* 269:543–546 (1995).
Hellman B. et al., "Endocrine Activity of the Testis in Obese–Hyperglycaemic Mice," *Acta Endocrinologica* 44:20–26 (1963).
Hellman, B., "Studies in Obese–Hyperglycemic Mice," *Ann. New York Acad. Sci.* 131(1):541–558 (1965).
Hummel, K.P., "Transplantation of Ovaries of the Obese Mouse," *Anat. Rec.* 128(3):569 (1957).
Ingalls, A.M. et al., "Obese, A new Mutation in the House Mouse," *J. Heredity* 41:317–318 (1950).
Kennedy, G.C. et al., "Body Weight and Food Intake as Inititiating Factors for Puberty in the Rat," *J. Physiol.* 166:408–418 (1963).
Lane, P.W. et al., "Fertile, Obese Male Mice," *J. Heredity* 45(2):56–58 (1954).
Maffei, M. et al., "Leptin levels in human and rodent: Measurement of plasma leptin and ob RNA in obese and weight–reduced subjects," *Nature Medicine* 1(11):1155–1161 (1995).
Pelleymounter, M.A. et al., "Effects of the obese Gene Produce on Body Weight Regulation in ob/ob Mice," *Science* 269:540–543 (1995).
Runner, M.N. et al., "Inherited hypofunction of the female pituitary in the sterile–obese syndrome in the mouse," *Genetics* 39(6):990–991 (1954).
Runner, M.N. et al., "Inherited hypofunction of the female pituitary in the sterile–obese syndrome in the mouse," *Records Genetics Soc. of America* 23:63–64 (1954).
Runner, M.N. et al., "Sterile, Obese Mothers," *J. Heredity* 45(2):51–55 (1954).
Smithberg, M. et al., "The Induction and Maintenance of Pregnancy in Prepuberal Mice," *J. Exper. Zoology* 133(3):441–457 (1956).
Smithberg, M. et al., "Pregnancy Induced in Genetically Sterile Mice," *J. Heredity* 48(3):97–100 (1957).
Stiff, M.E. et al., "Plasma Gonadotropins in Prenatal and prepubertal Female Mice: Disorganization of Pubertal Cycles in the Absence of a Male," *Endocrinology* 94(2):492–496 (1974).

(List continued on next page.)

*Primary Examiner*—Kimberly Jordan
*Attorney, Agent, or Firm*—Townsend and Townsend and Crew LLP

[57] ABSTRACT

A method for restoring reproductive function in a reproductively impaired male or female host is disclosed, the method comprising administering a leptin compound to the host for a time and in an amount sufficient to restore or enhance reproductive function. A method of accelerating the onset of puberty in a male or female host is also disclosed, the method comprising administering a leptin compound to the host for a time and in an amount sufficient to cause the onset of puberty.

26 Claims, 13 Drawing Sheets

OTHER PUBLICATIONS

Swerdloff, R.S. et al., "Reproductive Hormonal Function in the Genetically Obese (ob/ob) Mouse," *Endocrinology* 98(6):1359–1364 (1976).

Vigersky, R.A. et al., "Hypothalamic Dysfunction in Secondary Amenorrhea Associated with Simple Weight Loss," *N. Engl. J. Med.* 297(21):1141–1145 (1977).

Weigle, D.S. et al., "Recombinant ob Protein Reduces Feeding and Body Weight in the ob/ob Mouse," *J. Clin. Invest.* 96:2065–2070 (1995).

Zacharias, L. et al., "Sexual maturation in comtemporary American girls," *Amer. J. Obstet. Gynec.* 108(5):833–846 (1970).

Zhang, et al., "Positional cloning of the mouse obese gene and its human homologue," *Nature* 372:425–432 (1994).

METHODS FOR RESTORING OR ENHANCING REPRODUCTIVE FUNCTION IN REPRODUCTIVELY IMPAIRED HOSTS

This work was partly supported by NIH grant HLS 53762. The U.S. Government may have certain rights in this invention.

This application claims priority under 35 U.S.C.119(C) to provisional application 60/006,106, filed Oct. 25, 1995.

BACKGROUND OF THE INVENTION

The sterility of male and female homozygous ob/ob mice was recognized since the original report of the ob mutation (Ingalls et al. *J. Hered.* 41:317–318 (1950)). ob/ob females are always sterile whereas ob/ob males can occasionally become fertile if maintained on a restricted diet (Lane et al. *J. Heredity* 45:56–58 (1954)). The ovaries of ob/ob females are capable of producing viable eggs when transplanted into lean female recipients (Hummel et al. *Anat. Rec.* 128:569 (1957)). Although early sexual development is normal, ovulation never follows and the mice remain prepuberal indefinitely. FSH, LH and testosterone levels are reduced in ob/ob females (Swerdloff et al. *Endocrinology* 98:1359–1364 (1976)), demonstrating the absence of a functional feedback from the hypothalamic-pituitary axis. Hypofunction of the pituitary gland in the female ob/ob mouse was demonstrated indirectly by showing that their in vivo uterine weights did not significantly change after bilateral ovariectomy (Runner et al. *Genetics* 39:990–991 (1954); Drasher et al. *J. Heredity* 46:209–212 (1955)) but did, however, respond to exogenous estrogen. Pituitary extracts administered to ob/ob females induced ovulation and conception, but not implantation (Runner, M. N. *Rec. Genet. Soc. Am.* 23:63–64 (1954)) which was achieved following treatment with gonadotropic hormones (Runner et al. *J. Heredity* 45:51–55 (1954)). Furthermore, the administration of high doses of progesterone maintained pregnancy for 19 days p.c., but did not enable the mothers to deliver the fetuses except after administration of relaxin which stimulated parturition and lactation (Smithberg et al. *J. Exp. Zool.* 133:441–458 (1956); Smithberg et al. *J. Heredity* 48:97–100 (1957)). The above findings demonstrated that the sterility of the ob/ob female is caused by an insufficiency of hormones at the hypothalamic-pituitary level rather than physical hindrance of copulatory activity by excess adipose tissue.

Kennedy and Mitra (*J. Physiol.* (London) 166:408 (1963)) proposed that puberty is linked to body weight and more specifically to fat storage which is as they conclude, one of the signals responsible for the initiation of hypothalamic control of ovarian function. Frisch and McArthur (*Science* 185:949 (1974)) related the loss or restoration of menstrual cycles in young girls to a minimum weight for height and reported that normal girls become relatively fatter from menarche to reproductive maturity. Therefore, these early and important findings established a relationship between initiation of reproduction and adiposity. In support of this relationship were the observations that very lean young female ballet dancers and college rowers (Frisch et al. *NEJM* 303:17 (1980); Frisch et al. *JAMA* 246:1559 (1981)) have delayed puberty, whereas obese girls have an acceleration of puberty (Zacharias et al. *Am. J. Obs. Gyn.* 108:833 (1970)). Furthermore, the amenorrhea of extremely lean women was attributed to loss of fat and hypothalamic dysfunction (Vigersky et al. *NEJM* 297:1141 (1977)). Based on these findings, a "critical weight" hypothesis was suggested (Frisch et al. *Science* 109:397 (1970)) extending the assumption that a metabolic signal may be responsible for the initiation of reproduction. Moreover, adipose tissue has been viewed not only as an energy source but also as a direct regulator of female reproduction (R. E. Frisch *Adipose Tissue and Reproduction Progress in Reproductive Biology and Medicine* vol. 14 (1990)) since it converts androgens to estrogens via aromatization (P. K. Sifteri *J.Endocrinology* 89:119 (1981)).

The cloning, expression, and biological activities of leptin, the ob gene product, were described in a number of references, such as Pelleymounter et al. *Science* 269:540–543 (1995); Halaas et al. *Science* 269:543–546 (1995), and Campfield et al. *Science* 269:546–549 (1995).

While a variety of hormonal and other treatments have been proposed for lack of fertility in males or females, none have been entirely successful, and there remains a need for identifying improved and/or alternative therapies for enhancing fertility. In particular, improved methods and compositions should be effective, have minimum side effects, optionally be compatible with other hormonal treatments, and contribute to conception, pregnancy maintenance, and/or delivery of viable fetuses. The instant invention addresses this need and more.

SUMMARY OF THE INVENTION

One aspect of the invention is a method for restoring reproductive function in a reproductively impaired male or female host, the method comprising administering a leptin compound to the host for a time and in an amount sufficient to restore or enhance reproductive function.

A further aspect of the invention is a method of accelerating the onset of puberty in a male or female host, the method comprising administering a leptin compound to the host for a time and in an amount sufficient to cause the onset of puberty.

The leptin compound is administered to a female host from a time prior to impregnation through delivery of offspring, and preferably through lactation. The leptin compound may be a recombinant protein comprising the full secreted form of leptin. In other embodiments the leptin compound may be a recombinant protein comprising at least a biologically active fragment of leptin. The leptin compound is administered in a dosage from about 0.1 ng/kg body weight to 100 mg/kg body weight, typically subcutaneously, intradermally, intravenously, intramuscularly, intraperitoneally, orally, transdermally, via pulmonary delivery, via intranasal delivery, via controlled release, or via pump. The leptin compound is typically administered continuously or in discrete doses. The male or female host may suffer from a physiological defect of one or more hypothalamic, pituitary, or gonadal hormones. The host may be obese or non-obese. In some embodiments the host has a body mass index of less than about 20.

DESCRIPTION OF THE PREFERRED EMBODIMENT

Figure 1:
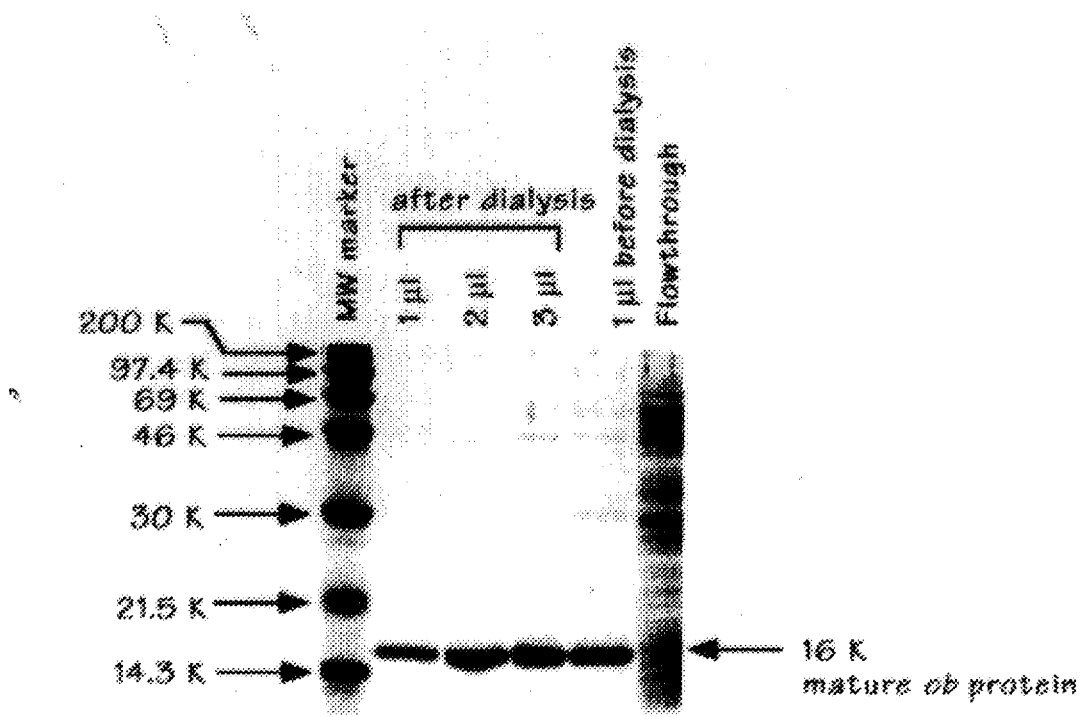
FIG. 1 depicts a 12% SDS-polyacrylamide gel showing 1 µl aliquots of the recombinant human leptin before and after dialysis and 2 µl and 3 µl after dialysis. A 1 µl aliquot from the metal chelate affinity column flow through shows bacterial proteins not bound to the column.

Exemplary methods for cloning and purifying leptin compounds are described in scientific literature. See, for example, Pelleymounter et al. *Science* 269:540–543 (1995); Halaas et al. *Science* 269:543–546 (1995), Campfield et al. *Science* 269:546–549 (1995), and Chehab et al. *Nat. Gen.* 12:318–320 (1996). Leptin compounds suitable for use in the present invention, also termed "leptin" herein, may comprise a full-length leptin polypeptide obtained from a mammalian source, preferably human for the treatment of humans. Typically, the leptin compound will be a recombinant polypeptide. The recombinant polypeptide can be produced in mammalian, bacterial, or yeast expression systems. Suitable leptin compounds may also comprise fragments, analogs, and derivatives, including truncated forms, of the full-length leptin polypeptide. Fusions of such compounds to a non-leptin polypeptide are included in the scope of the invention. In particular, a fusion protein incorporating the human leptin polypeptide used in the Examples section hereinafter, is at least one exemplary leptin compound which is suitable for use in the methods of the present invention.

Reproductively impaired female hosts suitable for treatment by the methods of the present invention will usually suffer from a deficiency in the hormonal system which supports ovulation, conception, maintenance of pregnancy, and/or delivery of offspring, typically being one or more hypothalamic, pituitary, or gonadal hormones. Administration of the leptin compound is believed to correct or help correct such deficiencies in the hypothalamic-pituitary-gonadal hormone system of the reproductively impaired female. "Reproductively impaired" is used interchangeably with infertile herein, and is intended to include amenorrheic females. Reproductively impaired females include those incapable of ovulation, conception, pregnancy maintenance, lactation, and/or delivery of full-term offspring, as well as those having difficulty in these areas. Administration of the leptin compound will restore and/or enhance the ability of such females to conceive and bear children. Similarly, infertile males include those incapable of impregnating females. "Sterile" is used interchangeably with "infertile" and "reproductively impaired" herein.

The male or female hosts treated by the method of the present invention may be obese or non-obese. It is believed that administration of the leptin compounds will restore hormonal function associated with obesity or gross alteration in body weight as well as other conditions which are not associated with obesity.

Thus, the present invention provides methods for restoring reproductive function in a reproductively impaired male or female host, the method comprising administering a leptin compound to the host for a time and in an amount sufficient to restore or enhance reproductive function. In some embodiments of this invention a leptin compound will be administered to a male or female host to accelerate the onset of puberty. "Puberty" as used herein includes the initiation and completion of the first menstrual cycle. Typically, the male or female host will have experienced a delayed onset of puberty or be at risk for a delayed onset of puberty, typically as a result of gross deviation in body weight, before treatment with a leptin compound. The leptin compound will usually be administered in a dosage from 0.1 ng/kg body weight to 100 mg/kg body weight. Amounts effective for this use will depend on, e.g., the leptin composition, the manner of administration, the weight and general state of health of the patient, and the judgment of the prescribing physician.

The leptin compound will typically be administered to a female host during at least a portion of the time from prior to impregnation through delivery of the offspring, usually during the entire period from prior to impregnation through delivery of the offspring, and preferably through lactation.

The leptin compound will typically be administered to a male host during at least a portion of the time from prior to impregnation of a female to when impregnation has been confirmed.

The leptin compound will typically be administered to a host experiencing a delayed onset of puberty for at least a period prior to the onset of puberty through puberty, and possibly through a period of desired impregnation and delivery of offspring, typically in an amount sufficient to cause the onset of puberty.

The treated male or female host is typically human, but the method is effective with other mammalian hosts, such as mice. The host will usually suffer from an insufficiency of one or more hypothalamic, pituitary, or gonadal hormones of the type necessary for or otherwise involved in reproductive fertility. In some cases the hosts will be obese; in other cases the hosts may be non-obese. obesity is defined as including having a body mass index (BMI; weight in kg/(height in meters)$^2$) over about 30. In some instances, the non-obese host will have a BMI of less than about 20.

The leptin compound may be administered subcutaneously, intradermally, intravenously, intramuscularly, intraperitoneally, via pulmonary delivery, via intranasal delivery, transdermally, orally, via controlled release, via pump, or by any other conventional route of administration for polypeptide drugs. Typically, the leptin compound will be administered continuously during the period of administration, i.e., being delivered at least once per day or via controlled release techniques, such as via transdermal patches.

In some embodiments, the invention provides compositions for administration which comprise a solution of leptin dissolved or suspended in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of leptin in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10%–95% of active ingredient, that is, one or more leptin compounds of the invention, and more preferably at a concentration of 25%–75%.

For aerosol administration, leptin is preferably supplied in finely divided form along with a surfactant and propellant. Typical percentages of leptin are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant. A carrier can also be included, as desired, as with, e.g., lecithin for intranasal delivery.

The leptin compositions of the invention can additionally be delivered in a controlled release system such as a depot-type system, an encapsulated form, or an implant by techniques well-known in the art. The compositions of the invention can also be delivered via a pump, such as a minipump, to the male or female host.

The following examples are offered by way of illustration, not by way of limitation.

EXAMPLES

I. Rescuing Fertility in Females
  A. Results and Discussion
  This study investigated the ability of leptin to correct the reproductive defect of the sterile female ob/ob mouse.
  The human ob cDNA sequences spanning amino acids 22 to 167 (Zhang et al. *Nature* 372:425–32 (1994)) and representing the secreted ob protein were cloned into the expression vector pQE30. The 16 Kd ob protein was overexpressed in *E.coli*, purified and renatured by dialysis (FIG. 1).

The refolded leptin protein was injected intraperitoneally into 2 groups of experimental ob/ob female mice at a dose of 10 µg/g of initial body weight. Control ob/ob mice were injected with identical volumes of phosphate buffered saline (PBS). The first group consisted of 4 ob/ob animals (2 controls and 2 experimentals) and the second group of 10 ob/ob animals (5 controls and 5 experimentals).

In the first group, the two experimental ob/ob female mice (ob-5 and ob-6), weighed respectively, 48.5 g and 51.7 g whereas the two control mice weighed 53.8 g and 50.0 g. In addition, 2 female db/db mice also received leptin injections to test for non-specific weight loss as these mice are resistant to leptin effects, presumably due to a defect in the leptin receptor (Coleman et al. *Am. J. Phys.* 217:1298–1304 (1969); Coleman, D. J. *Diabetoloqia* 9:294–298 (1973)). Food intake and body weights were continuously measured to determine the efficacy of the treatment.

Figure 2A:
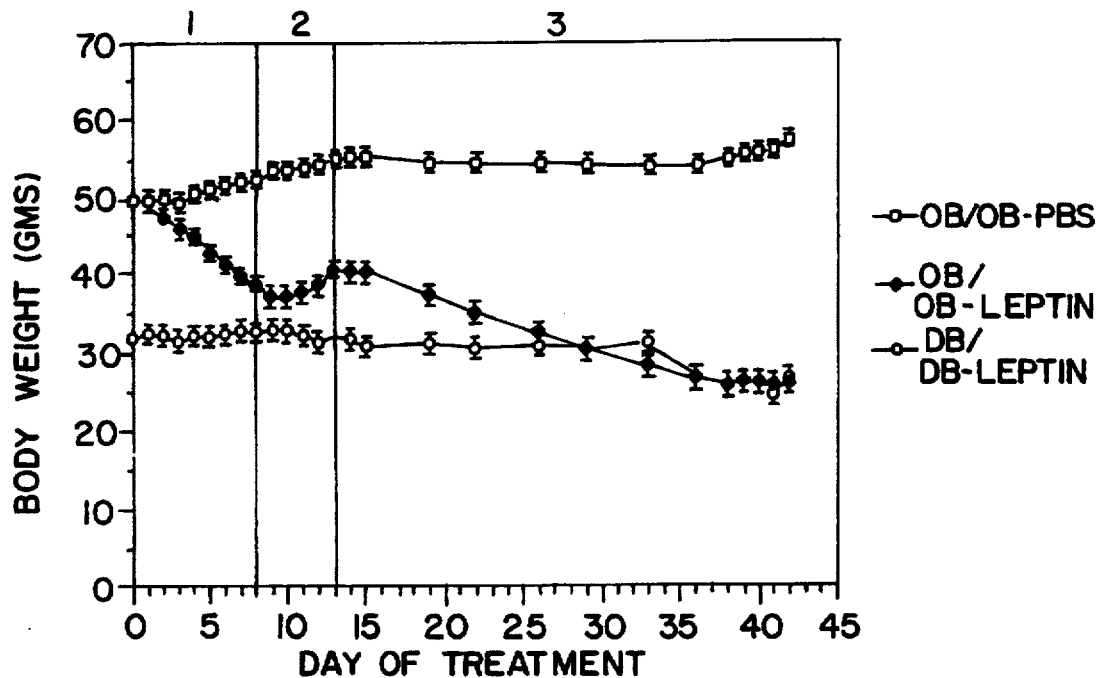
FIG. 2 depicts the body weights (a, b) and food intake (c, d) of ob/ob and db/db female mice during the 3 phases of leptin treatment for group 1 (a,c) and the single phase treatment for group 2 (b, d). In the first group, the 3 phases of the treatment are shown on top of each graph and outlined by vertical lines on each graph.
Figure 2B:
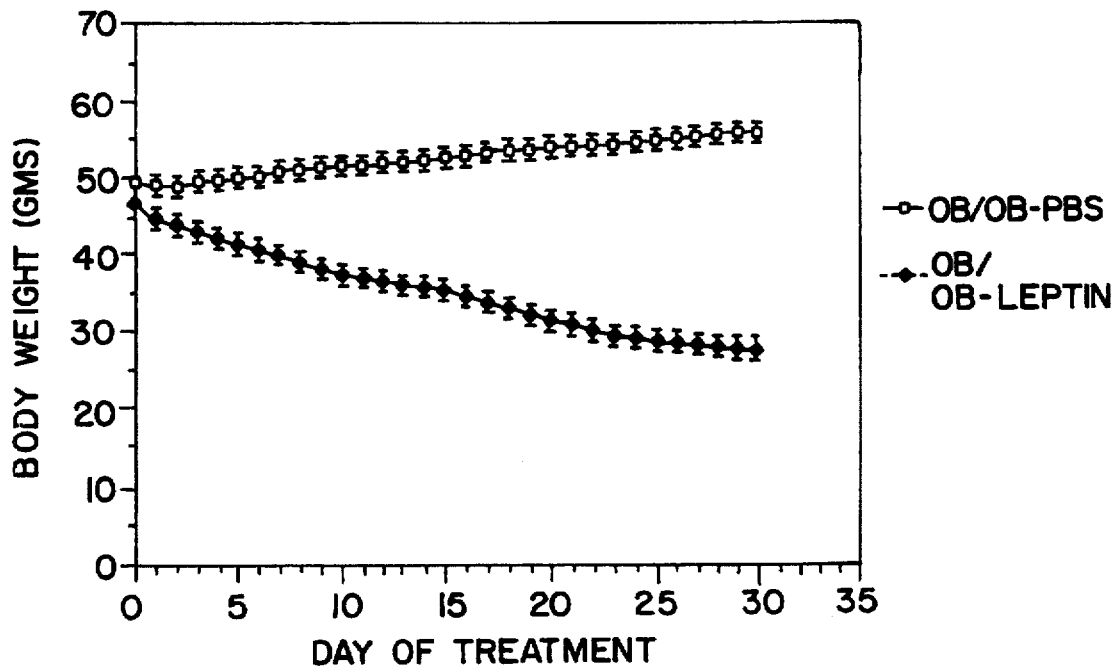

The leptin treatment for the first group consisted of 3 phases. In the first phase which lasted 8 days, the mice received two injections per day of PBS or leptin. At the end of the first phase, weight loss in the treated animals was 24% and 27% of their original body weight (FIG. 2A). In contrast, the body weights of both ob/ob PBS-controls and one leptin treated db/db mouse increased by 6% whereas the second db/db treated mouse lost 1% of body weight (FIG. 2A). Food intake of leptin treated ob/ob mice was markedly reduced to 13% of the food intake of control ob/ob mice (FIG. 2B). Withdrawal of the leptin injections in the second phase showed in the ob/ob mice, a rapid increase in food consumption and body weight, demonstrating the need for repeated leptin injections to maintain a biological effect (FIG. 2A and 2B). The third phase consisted of single daily leptin injections which produced a biological response similar to the first phase, albeit at a lower rate as evidenced by the slopes of the two body weight curves during phases 1 and 3 (FIG. 2A). Injections were continued for a total of 42 days in the two leptin treated ob/ob mice until their body weights stabilized to approximately 28 g and 25 g corresponding to 46% and 48% reductions in body weight. The body weights of the db/db mice changed minimally (FIG. 2A) whereas their food intake increased in parallel with that of PBS injected ob/ob controls (FIG. 2B).

Figure 2C:
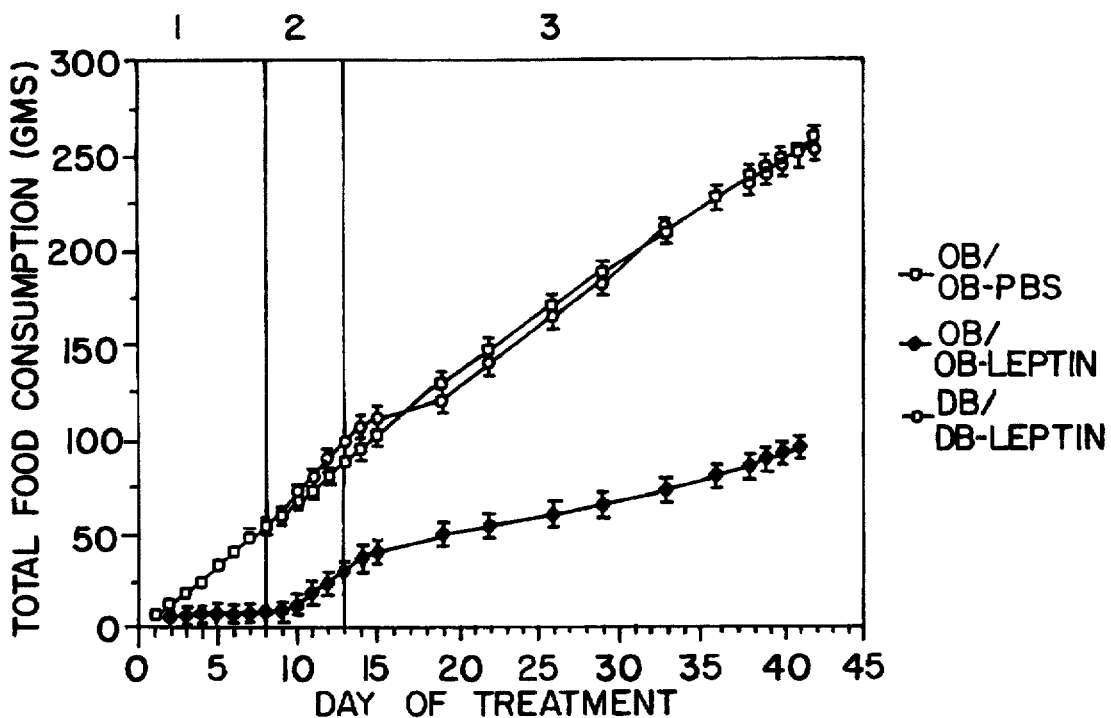
Figure 2D:
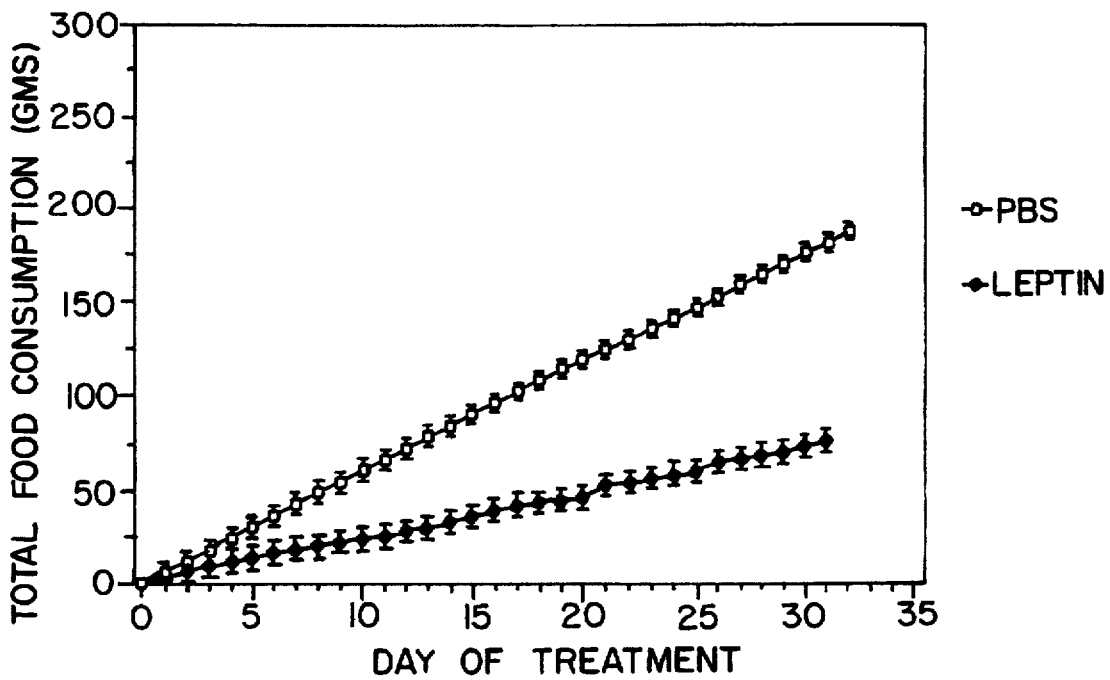

In the second group, the experimental ob/ob mice were injected intraperitoneally once daily with a 10 µg/g initial body weight of leptin for 30 days. The mean body weights of the 5 ob/ob controls after 30 days was 55.9±2.0 as compared to 27.8±0.9 for the 5 leptin treated ob/ob mice. The treated mice had lost 40% of their original body weight whereas the control mice increased their body weight by 13% (FIG. 2C and 2D).

Figure 3:
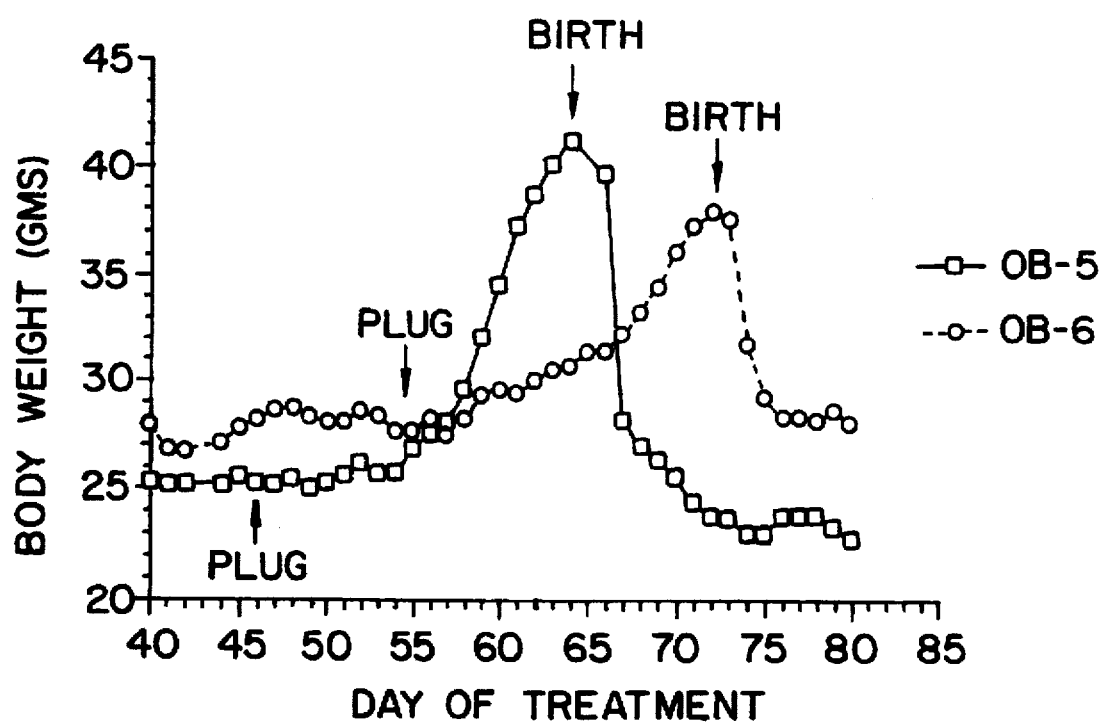
FIG. 3 depicts the body weight profiles of the two leptin treated ob/ob females after stabilization of their body weights and mating to a lean wild-type C57BL/6J male. The two mice showed copulatory plugs at days 46 and 54 of the treatment and gave birth at respectively, 64 and 73 days.

After 6 weeks of leptin treatment, at a time where body weight had stabilized, the 2 PBS-controls and 2 leptin-treated mice (ob-5 and ob-6) from the first group were mated with a normal C57BL/6J male mouse. A copulatory plug was detected only in ob-5 and ob-6 shortly thereafter, but not in the controls. The formation of copulatory plugs demonstrates the occurrence of estrus and ovulation in the treated ob/ob females. Leptin injections were then continued at half the original dose. The treated females started to show a significant increase in body weight at day 12 p.c. and delivered newborn pups at 20.5 and 19.5 days p.c. (FIG. 3). Parturition occurred in both treated mice over at least 36 hours resulting in the delivery of 6 (ob-5) and 2 (ob-6) pups.

Figure 4:
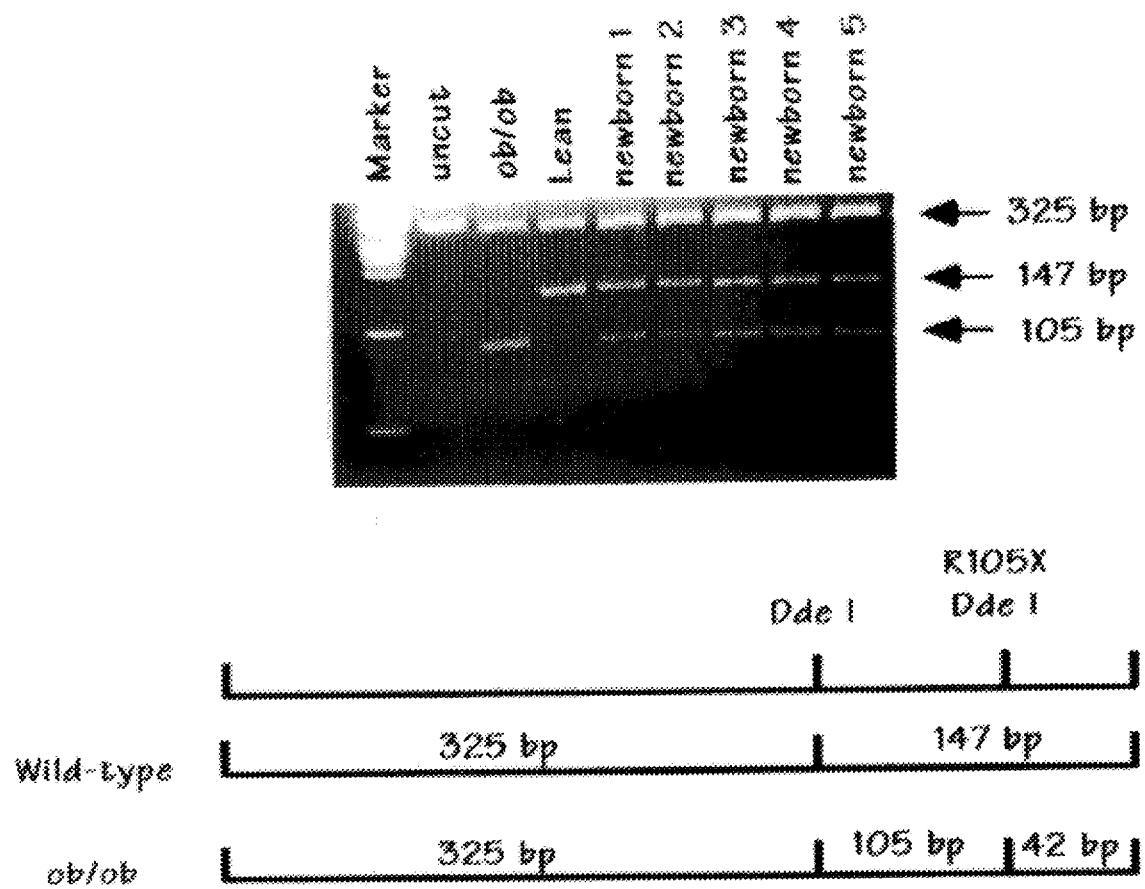
FIG. 4 depicts the PCR allele-typing of the R105X obesity mutation. The 8% polyacrylamide gel shows PCR products cleaved with Dde I from the homozygous C57BL/6J lean father, a leptin-treated homozygous ob/ob mother and their 5 newborn mice. The 472 bp PCR product generates upon cleavage with Dde I a constant 325 bp fragment and a 147 bp fragment diagnostic of the wild-type allele and 105 bp and 42 bp fragments diagnostic of the mutant ob allele. The newborn mice are all heterozygous at the ob locus as shown by the presence of both 147 bp and 105 bp fragments. The 42 bp fragment is off the gel. The DNA marker is ΦX cleaved with Hae III.

Although the mice were alive and fully developed at birth, none of the newborns survived. Five intact or partially eaten newborn mice were recovered from ob-5 and 2 mice from ob-6. DNA was extracted from the newborns to determine their genotypes at the ob locus. PCR primers bracketing codon 105 which is the site of the mutation in the ob/ob mouse, were designed and used for DNA amplification. The 472 bp amplified PCR product contains in the homozygous normal mouse a single Dde I site which produces 325 bp and 147 bp fragments upon cleavage with Dde I. However, the R105X obesity mutation generates an additional Dde I site which results in fragments of 325 bp, 105 bp and 42 bp in the homozygous ob/ob mouse. PCR testing showed that the lean male mouse who fertilized both treated females was homozygous for the wild-type allele, whereas both mothers were homozygous for the mutation and all newborn mice were heterozygous for R105X (FIG. 4).

In the second group, 4 ob/ob controls and 4 ob/ob leptin-treated mice whose body weight stabilized as a result of the leptin treatment were also mated to C57 BL/6J wild-type lean males. All 4 leptin-treated, but not any of the control ob/ob mice, became pregnant. Furthermore, ob-5, who was under continuous leptin treatment even after delivery, became pregnant a second time, demonstrating that the entire process can be repeated.

Although the levels of reproductive hormones in the pregnant females were not measured, the entire process of ovulation, pregnancy and parturition could not have occurred in the absence of these hormones. The previous findings that the ob/ob females can respond to the effects of these hormones either exogenously or in vivo after ovarian transplants demonstrates that leptin can stimulate the production of hormones required for ovulation, pregnancy and parturition. Furthermore, these studies show that the sterility defect in adult ob/ob female mice is a reversible process that can be corrected with leptin treatment. Therefore, leptin is not only a satiety factor that can suppress appetite and promote lipolysis (Pelleymounter et al. *Science* 269:540–543 (1995); Halaas et al. *Science* 269:543–546 (1995); Campfield et al. *Science* 269:546–549 (1995); Weigle et al. *J. Clin. Inv.* 96: 2065–2070 (1995)) but also plays an important role in reproductive physiology.

It is not clear why the newborn mice were eaten by the mothers. It is possible that daily handling and injection of the mothers throughout gestation and especially before and after delivery is a contributing factor to this effect. It is also possible that the mothers failed to nurse the newborns, from possibly a lack of prolactin secretion.

Rescue of the sterility phenotype in ob/ob females has important implications for the husbandry of this strain. Whereas ovarian transplants have been a successful approach to the maintenance and propagation of the ob/ob strain, an alternative solution, leptin treatment, is available as a result of the studies described herein.

B. Methods

1. Expression and purification of the recombinant human ob protein.

Human ob cDNA sequences representing the mature secreted human protein (from amino acids 22 to 167) were amplified by RT-PCR from normal human fat mRNA using human specific cDNA primers based on the Genbank sequence U18915. The cDNA was subcloned by blunt-end ligation into pSK+ srf (Stratagene), recovered as a Bam HI restriction fragment and inserted into the expression vector pQE30 (Quiagen). The recombinant ob protein was thus under the control of a T5 bacteriophage promoter, had a hexahistidine tag at the amino terminus and a stop codon immediately following amino acid 167. The DNA construct was transformed and overexpressed in *E. coli* following induction by IPTG. A crude protein lysate was prepared under denaturing conditions and the ob protein purified by metal chelate affinity chromatography on a nitrilo-tri-acetic acid (NTA) resin. The bound protein was finally eluted and recovered in 20 ml o 4.6M urea, 0.077 M Na2HPO4, 0.077M Tris pH 8.0 and 250 mM imidazole. The eluted protein was allowed to refold by slow dialysis of the denaturant successively in 4 M, 3 M, 2 M, 1 M, 0.5 M urea in phosphate buffered saline (PBS). Final dialysis was in 3 changes of PBS. Each dialysis step was performed for at 12-24 hours in 6000-8000 molecular weight cutoff (MWCO) tubing at 4° C. against 50 volumes of solution. Aliquots of the refolded protein were used to determine its concentration by the Bradford protein assay (Biorad Laboratories). In addition, purity and recovery of the protein after dialysis were estimated by fractionation on a 12% stacking SDS-polyacrylamide gel. Electrophoresis was performed at 100V, 25 mA for 2 hours in 25 mM Tris, 250 mM glycine and 0.1% SDS. The gel was then stained with Coomassie Blue and extensively destained in 45% methanol, 10% acetic acid.

2. Leptin treatment of the ob/ob mice.

Homozygous female C57BL/6J-ob/ob and C57BL-KsJ-db/db mice were purchased from the Jackson Laboratories and housed at the UCSF Animal Care Facility under alternating 12-hours light and dark periods.

For the first group of mice, the initial phase of the treatment (days 1-8) consisted twice daily (between 8-9 a.m. and 5-6 p.m.) of either PBS or recombinant human leptin injections at a dose of 10 µg/g of initial body weight. In the second phase (days 9-13), injections were completely withdrawn and in the third phase, which began at day 14, the mice received a single injection (between 5-6 p.m.) per day of either PBS or leptin. The second group received once daily a 10 µg/g of initial body weight dose throughout the single phase treatment. The dose of leptin was reduced to half upon observation of the copulatory plug and continued at a single injection daily throughout gestation until delivery. The mice were weighed periodically and food consumption deduced by weighing the food left in the cage at periodic intervals. The dead newborn mice were frozen at -20° C. until DNA extraction.

3. Genotyping of the newborn mice.

5 mm sections from the frozen embryos or tail of the ob/ob mother and lean father were obtained by excision. The tissue was first homogenized in 10 mM Tris-1 mM EDTA (TE) to generate a cell suspension. SDS was then added to 0.5% to lyse the cells and the mixture extracted with phenol-chloroform followed by ethanol precipitation. The DNAs were dissolved each in 50 µl of TE and 5 µl aliquots subjected to DNA amplification by the polymerase chain reaction (PCR). The PCR primers consisted of 5' CTGGT-TCTTCACGGATATCATTG 3' and 5' AGGGAG-CAGCTCTTGGAGAA 3'. The amplification reaction was carried out in 50 µl for 35 cycles at 95° C., 55° C. and 72° C. for 30 sec. after which a discrete 472 bp product was obtained. A 7 µl aliquot was then digested with Dde I (New England Biolabs) and the digested products fractionated on a native 8% polyacrylamide gel. The gel was stained with ethidium bromide and the products visualized under ultraviolet light.

II. Triggering of reproductive function in prepuberal normal female mice

This study demonstrated that leptin is a critical signal for the initiation of reproduction. Without being limited to any one theory, leptin may stimulate GnRH release so as to initiate puberty.

A. Measurement of Leptin Half-life

An advantage of using human leptin for these experiments lies in the ability to measure independently mouse endogenous and human exogenous leptin with specific radioimmunoassays that have virtually no cross reactivity with each other (<0.2%). Measurement of leptin levels with the human specific radioimmunoassay revealed undetectable levels in control mice, thus demonstrating the specificity of the assay.

The clearance time of exogenous human recombinant leptin was determined to calculate the frequency of injections in subsequent experiments as follows. Twenty eight C57 BL/6J adult females weighing 24.1±0.7 g, fed ad lib., were divided between a control and a leptin group. Six mice were injected with PBS vehicle solution and 21 others with a 4 µg/g body weight dose of immunoreactive leptin. Control mice were sacrificed immediately after saline injection whereas 3 leptin-injected mice were sacrificed at each 1, 2, 3, 4, 5, and 7 hours. Blood was collected by cardiac puncture and the plasma separated by centrifugation and frozen at -20° C. until use.

Figure 5:
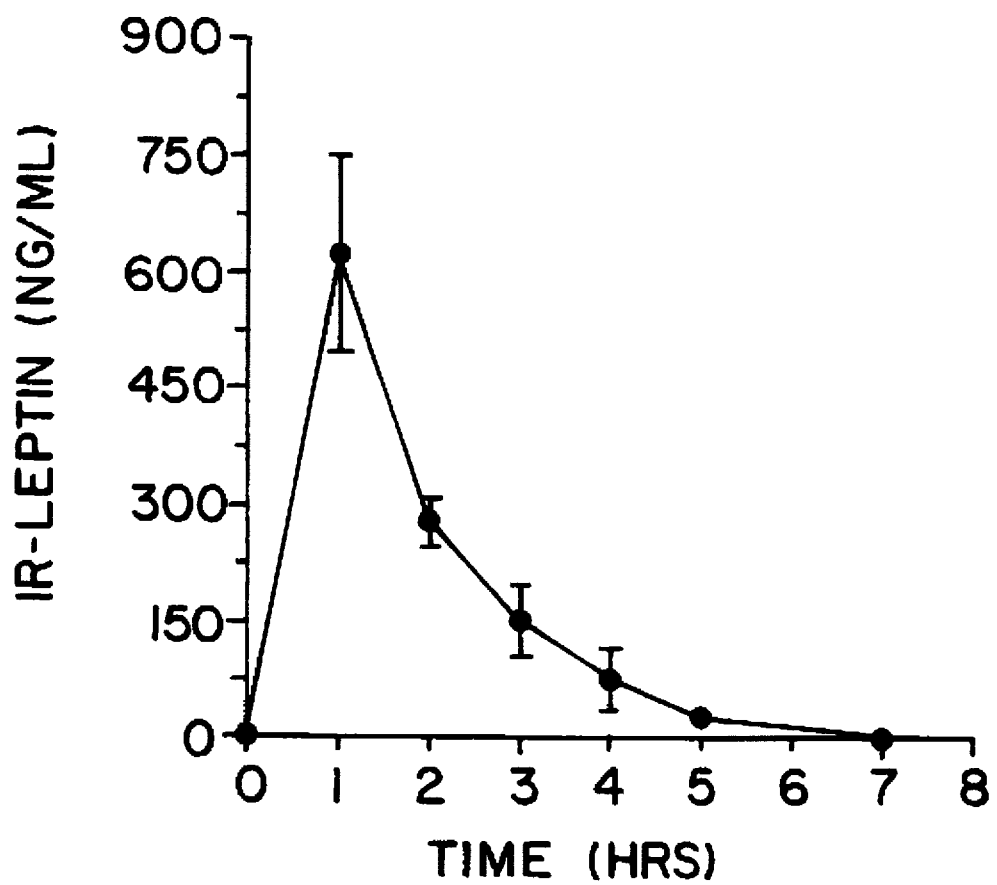
FIG. 5 depicts the time course of leptin clearance from the circulation of lean C57BL/6J females. Each point represents the mean ±SEM concentration of immunoreactive (IR) leptin in 3 adult females sacrificed at the indicated time. None of the 6 controls injected with PBS for the 0 time point had any detectable human leptin in their circulation, thus denoting the high specificity of the assay for human leptin on a mouse background. Note that leptin concentrations drop by almost 50% every hour, suggesting that the half-life of leptin is approximately 1 hour.

In the injected animals, immunoreactive leptin (IR-L) peaked at 1 hour and started to decline approximately by 50% each hour until it was undetectable at 7 hours post injection (See FIG. 5). Therefore, leptin has a half-life of approximately 1 hour. Consequently, leptin was administered daily in subsequent experiments between 5-7 p.m. just prior or soon after the onset of the dark period.

Because previous studies have shown that large amount of exogenous leptin are required to exert a biological effect in normal C57BL/6J mice (Pelleymounter et al. *Science* 269:540 (1995); Halaas et al. *Science* 269:543 (1995)), exogenous leptin was administered in these experiments at 2 µg/g body weight (half the dose used in the clearance study).

B. Fertility of leptin-treated lean female mice

To determine whether leptin-treated mice will reproduce earlier than control animals, fertility was selected as an endpoint of the experiment. The rationale of this study was derived from the hypothesis that if fat is a determinant for puberty, then leptin, which is secreted from fat may be a critical factor in initiating reproductive function. Therefore, treatment of prepuberal mice with exogenous leptin would "trick" neuroendocrine pathways involved in reproduction into acting as if the animal accumulated a certain amount of fat as reflected by the elevated levels of leptin in its circulation.

Prepuberal C57BL/6J mice (n=25) were weaned at 21 days of age and divided into two groups. One group (n=13) weighing 10.2±0.4 g received one daily injection of the human recombinant leptin whereas the other group (n=12) weighing 10.3±0.3 g received identical volumes of the phosphate buffered-saline (PBS) vehicle solution. Breeder males were then placed at day 28 in each cage at a ratio of one male per 3 females until a copulatory plug was detected in each female whose weight and age was recorded. Plugged females were kept under either treatment until 20 days after detection of the plug and were housed each in a separate cage to assess whether the copulatory plug was associated with a successful pregnancy.

All procedures were approved by the UCSF Committee on Animal Research. Two-week-old lactating prepuberal C57 BL/6J female pups were obtained from the Jackson Laboratories and allowed to recover for one week prior to initiation of the experiment. All male pups were removed from the litters at 2 weeks of age. Mice were housed at the UCSF Animal Care Facility and maintained at 20° C. with a 12 hrs. light, 12 hrs. dark cycle (lights on at 6 a.m., off at 6 p.m.). Mice were treated with human recombinant leptin as described above. The leptin preparation was quantitated by radioimmunoassay (Linco Research, St. Louis Mo.) and injected intraperitoneally at a dose of 2 µg/g body weight while control animals received phosphate buffered saline (PBS) injections. Prepuberal C57BL/6J mice (n=25) born on the same day were weaned at 21 days of age and housed in 7 cages consisting each of 3 mice and 1 cage of 4 mice. Animals from the same litter were placed into different cages such that no cage contained two mice from the same litter and divided into two groups. One group (n=13) weighing 10.2±0.4 g received one daily injection of 2 µg/g body weight IR-L whereas the other group (n=12) weighing 10.3±0.3 g received identical volumes of the phosphate-buffered-saline (PBS) vehicle solution. The mice were continuously monitored for body weight, food intake and vaginal opening which occurred in both groups at 26–27 days of age. Young female mice were housed away from males and had no contact with males or their urine until day 28, when a sexually competent adult C57 BL/6J male was added to each of the 8 cages at a ratio of one male per 3 females to initiate mating. Plugged females were kept under either treatment until 20 days after detection of the plug and were housed each in a separate cage to assess whether the copulatory plug was associated with a successful pregnancy. All statistical P values in this study were calculated by two-sample t-test using a Macintosh computer equipped with statistical package.

Figure 6A:
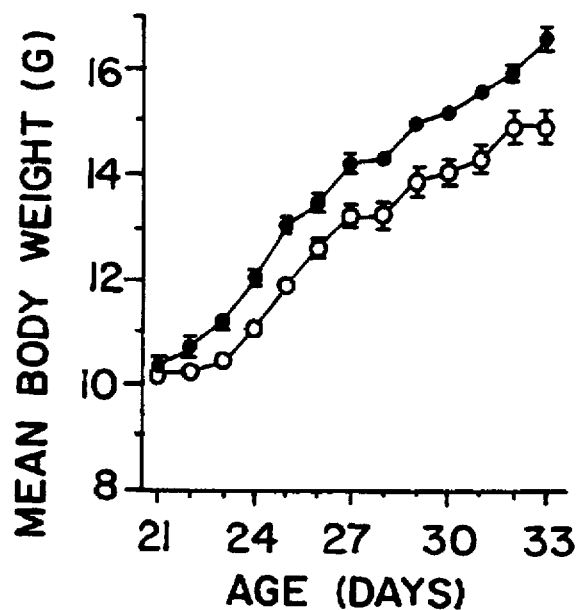
FIG. 6 depicts the effect of leptin treatment on body weight (A) and food intake (B) of prepuberal female mice. Either vehicle (solid circles) or leptin (open circles) treatment was initiated at 21 days of age when the animals were weaned. The addition of breeder males to both groups on day 27 resulted in a slight stabilization of body weight. Total food intake (B) was reduced by approximately 18% during the 6 days of treatment prior to the addition of the breeder males.
Figure 6B:
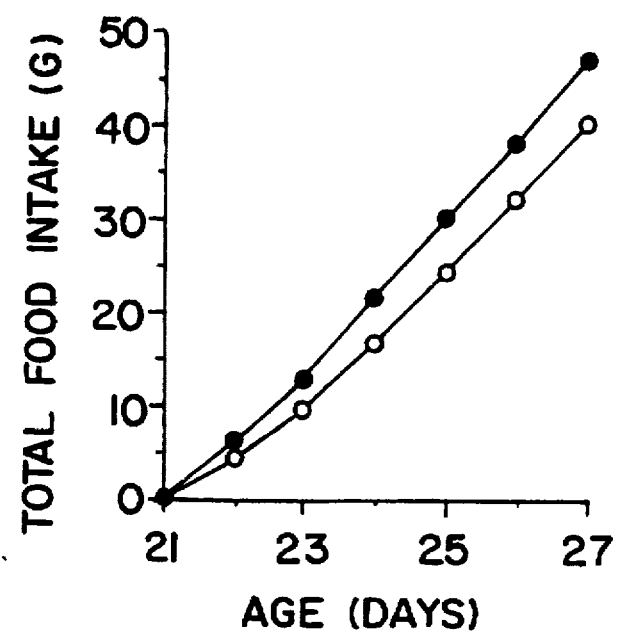

Leptin treatment of the young mice resulted in a slow-down of growth as compared to the control group (FIG. 6A) and was statistically significant from the third day (P=0.003) and throughout the treatment. This effect was primarily due to a decrease in food intake, as shown in FIG. 6B.

Figure 7A:
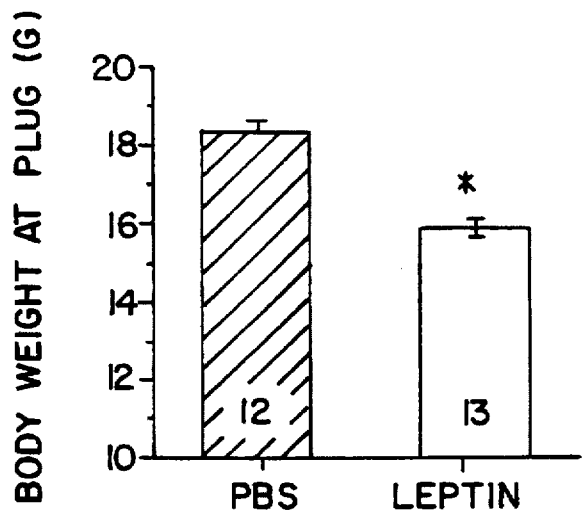
FIG. 7 depicts the acceleration of reproduction in leptin (white bar) versus vehicle-treated (black bar) mice. The number inside the bars represent the number of mice in each group. (A) Body weights of females at the time the copulatory plug was detected. PBS-treated mice had a mean body weight of 18.3±0.3 g versus 15.9±0.2 g for the leptin-treated group (P<0.001 by student's t-test is denoted by the asterisk). (B) Percentage and age of mice with a copulatory plug in the PBS and leptin groups. Mice were compared at 3 age ranges of 30–39, 40–49 and 50–62 days of age. The asterisk denotes the statistical value of P=0.003 as determined by student's t-test at 30–39 days of age. The age distribution of the leptin-treated mice is shifted to the left reflecting an earlier age of mating behavior. (C) Percentage of plugged mice from each group that delivered pups. 42% and 46% of plugged PBS and leptin-treated mice resulted in deliveries of newborn pups.
Figure 7B:
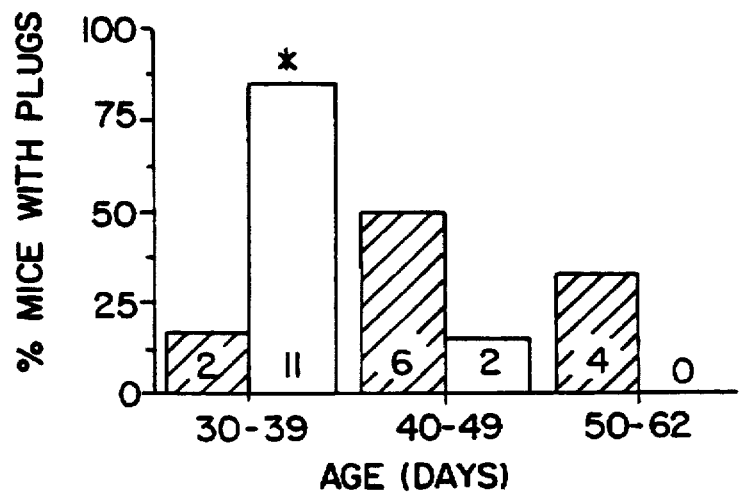

If leptin is involved in signaling puberty and the onset of reproduction, then leptin-treated mice, despite having a lower body weight (but high leptin levels) as a result of the thinning effects of leptin, will attain reproductive maturity earlier than the vehicle treated group. Indeed, these results showed that at the time the copulatory plug was first detected, leptin-treated mice had reached a body weight of 15.9±0.2 g as opposed to 18.3±0.3 g for the vehicle group (FIG. 7A), accounting for a 13% difference in body weight (P<0.0001). Furthermore, leptin-treated mice were plugged at an earlier age than the vehicle treated group. Thus, between the ages of 30–39 days, plugs were detected in 85% of leptin-treated mice (11 of 13 mice, P=0.003) and 17% (2 of 12 mice) of vehicle treated mice. The remaining 2 leptin-treated mice (15%) were plugged at 44 and 46 days of age as opposed to 40–49 and 50–62 days of age for respectively 6 (50%) and 4 (33%) of vehicle-treated mice (FIG. 7B).

Therefore, leptin treatment resulted in a significant acceleration of behavioral estrus and mating capability when the copulatory plug was used as a reproductive index. Thus, the attainment of the appropriate age and weight that allows initiation of reproduction in the control group, is advanced in the leptin-treated group owing to the elevated levels of leptin that have signaled neuroendocrine pathways that the animal has accumulated enough fat since leptin was shown to be a brain marker for adiposity (Frederich et. al. *Nat. Med.* 12:1311 (1995); Maffei et. al. *Nat. Med.* 11:1155 (1995)).

Figure 7C:
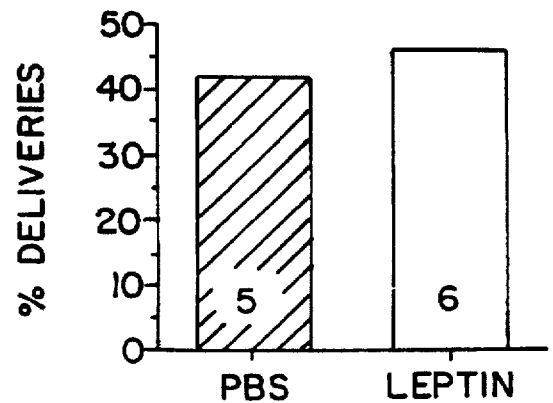

The proportion of plugged mice from both groups that carried out successful pregnancies at their first estrus was determined by delivery of newborn pups. Thus successful pregnancies and deliveries were comparable in both groups and consisted of 42% and 46% in vehicle and leptin groups, respectively (FIG. 7C). Altogether, leptin treatment resulted not only in an acceleration of behavioral estrus and mating but was also accompanied with normal pregnancies and deliveries, demonstrating successful ovulation among the leptin-treated mice.

To assess whether leptin treatment affected maturation of the reproductive tract in prepuberal mice, we determined in vehicle and leptin groups the timing of vaginal opening, initiation and progress of the first estrous cycle, the weights of uteri, ovaries and oviducts (which are excellent indices and bioassays of hormones action as well as LH and estradiol levels). Mice were weaned at 21 days of age and separated into PBS (n=12) and leptin (n=12) groups. Twenty four C57 BL/6j females were weaned at 21 days as above from different litters and divided equally with respect to litter of origin into vehicle (n=12) and leptin groups (n=12). Three animals were housed per cage with no litter mates placed in the same cage. The mice were treated with either PBS or leptin as above for 8 days and sacrificed on day 29 to collect blood, ovaries, oviducts and uteri. Dissection of each organ was carried out under a binocular microscope to ensure removal of contaminating tissues. Organs were weighed on a Metler AE160 high precision analytical balance.

Figure 8A:
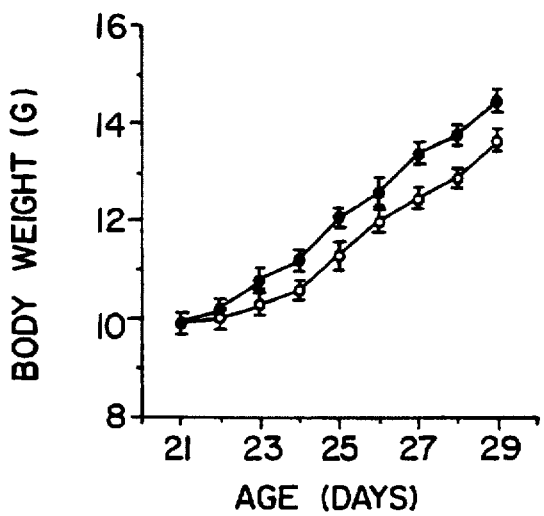
FIG. 8 depicts the effects of exogenous leptin on body weight (A), vaginal opening (B), onset of estrous cycle (C), uteri, oviducts and ovaries (D), LH (E) and 17-0-estradiol (F) in vehicle (O or black bar) and leptin (O or open bar) treated-group. A, B and C reflect continuous measurements from 21 to 29 days of age whereas D, E and F show determinations performed at the time of sacrifice. Asterisks denote statistical significance by student's t-test. Uteri, P<0.004; ovaries, P<0.0001; oviducts P=0.001; LH, P=0.007. D2, P, E and D1 denote respectively dipstrus, proestrus, estrus and metestrus.
Figure 8B:
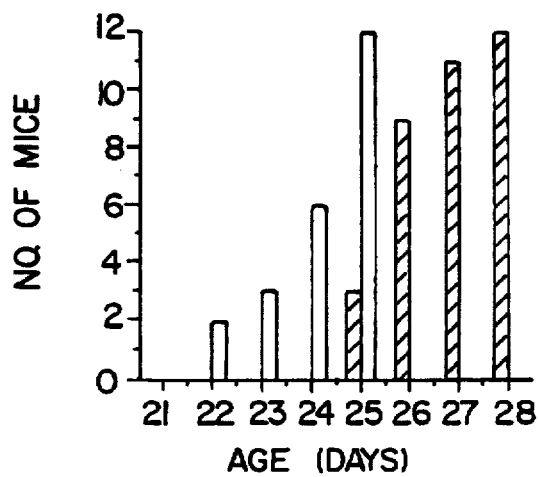

Leptin treated mice grew at a slower rate than vehicle treated animals, demonstrating again the effect of leptin on body weight (FIG. 8A). At the reproductive level, vaginal opening occurred in respectively 2, 1, 3, and 6 leptin-treated mice at respectively 22, 23, 24 and 25 days of age. However vaginal opening occurred in 3, 6, 2 and 1 vehicle treated mice at respectively 25, 26, 27 and 28 days of age (FIG. 8B). Thus vaginal opening is advanced up to 4 days as a result of leptin treatment.

Figure 8C:
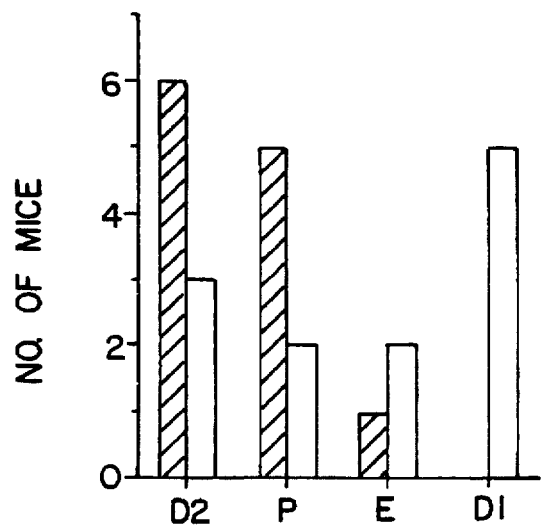

As a consequence of early vaginal opening, normal cyclicity was initiated in leptin treated mice prior to the control group (FIG. 8C) such that by day 29, 5 out of 12 leptin-treated mice had passed through estrus and progressed to metestrus (D1) stage thereby completing their first estrous cycle whereas none of the mice in the control group had reached that point. Mice, not exposed to males, have normally their first fully cornified smear 5–8 days after vaginal opening (Stiff et al. *Endocrinology* 84:492 (1974)).

A corollary of this experiment and the fertility experiment described above demonstrated that the biological actions of estrogens that are first evidenced by vaginal opening are not sufficient to elicit reproduction in control mice. However, in the experimental group, the presence of elevated levels of leptin with endogenous estrogens induce a rapid onset of reproduction. Thus, vaginal opening in mice lacking leptin is a sensitive index of estrogens action but not of fertility, whereas in leptin-treated mice, vaginal opening is associated with fertility.

Figure 8D:
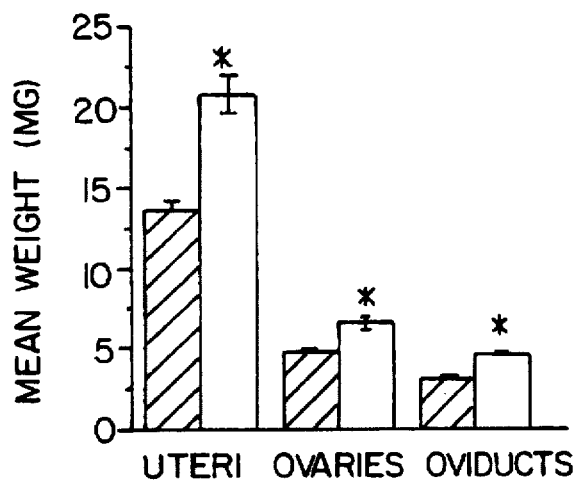

Evidence of gonadal steroids action was determined by assessing the weights of reproductive organs which are targets for hormones that are released transiently, but that produce long term effects on target tissues. Thus, the action of estradiol can be best evidenced by its striking and stimulatory effects on the hypertrophy and hyperplasia of uterine tissues thereby promoting uterine growth. In leptin-treated prepuberal mice, uterine weights consisted of 20.8±2.1 mg as opposed to 13.6±0.8 mg in controls (P=0.004) representing a 53% increase. Similar effects were found on ovarian (4.8±0.2 mg for vehicle vs. 6.6±0.3 mg for leptin. P<0.0001) and oviducts weights (3.2±0.2 for control vs. 4.6 ±0.3 for leptin, P=0.001) which increased respectively by 37.5% and 43.8% as a result of leptin treatment (FIG. 8D). Therefore, leptin treatment of the mouse at an early age resulted in a premature release of the hormones necessary for maturation of the reproductive tract.

Figure 8E:
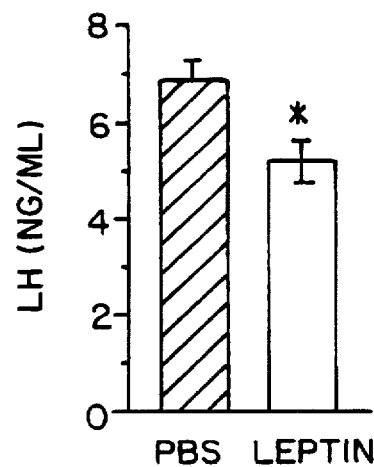
Figure 8F:
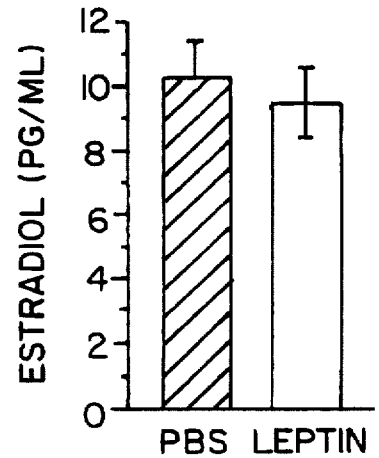

Hormone levels for the gonadotropin LH and the gonadal steroid 17-β-estradiol were determined at day 29, when the mice were sacrificed. LH was assayed on 50 μl plasma using a rat specific immunoassay purchased from Peninsula Laboratories (Belmont, Calif.). 17-β-estradiol levels were determined on 200 μl plasma by an ultrasensitive radioimmunoassay purchased from Diagnostic System Laboratories (Webster, Tex.). Unknown samples from both assays fell into the linear portion of each standard curve. LH levels consisted in control and leptin-treated mice of respectively, 6.9±0.4 ng/ml and 5.2±0.4 ng/ml, a statistically significant decrease (P=0.007) of 24.6% (FIG. 8E). However, 17-β-estradiol levels were comparable in both groups and consisted respectively of 10.3±1.1 pg/ml and 9.5±1.1 pg/ml for control and leptin-treated groups (FIG. 8F). Altogether, the results displayed in FIG. 8 show that leptin treatment of prepuberal mice causes at the reproductive level a concomitant stimulation of vaginal opening and ensuing first estrous cycle. These effects were mediated by the target actions of gonadal steroids which caused the reproductive tissues to mature earlier in leptin-treated mice. Because at the time of sacrifice, most control animals had not already ovulated, the findings that LH levels are elevated in control animals are consistent with the rising levels of LH prior to ovulation.

Conversely, the depressed levels of LH in leptin-treated animals reflect the completion or near completion of their first estrous cycle. Taken in this context, 17-β-estradiol levels thus reflect antiparallel effects whereby estrogen levels are on the rise in control animals that are progressing towards completion of their first cycle but decreasing in most leptin-treated mice that have already proceeded either close to or beyond their first cycle.

Figure 9A:
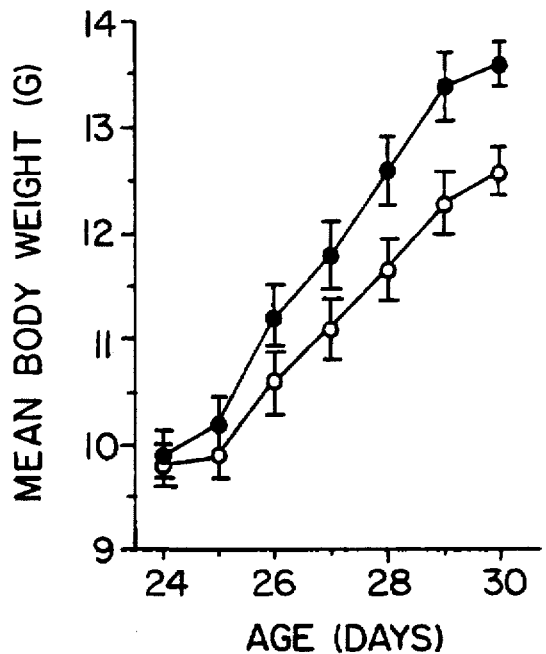
FIG. 9 depicts the effect of human recombinant leptin treatment on body weight and endogenous mouse leptin levels. (A) Body weights of prepuberal mice treated either with vehicle (O, n=12) or leptin (O, n=12). (B) 4 mice from each group were sacrificed at 30, 35 and 39 days of age to collect blood for endogenous leptin level measurements. Each time point represents the mean and SEM of 4 mice. The asterisk denotes statistical significance of leptin levels between 30 and 39 days of age (P=0.015 by student's t-test).
Figure 9B:
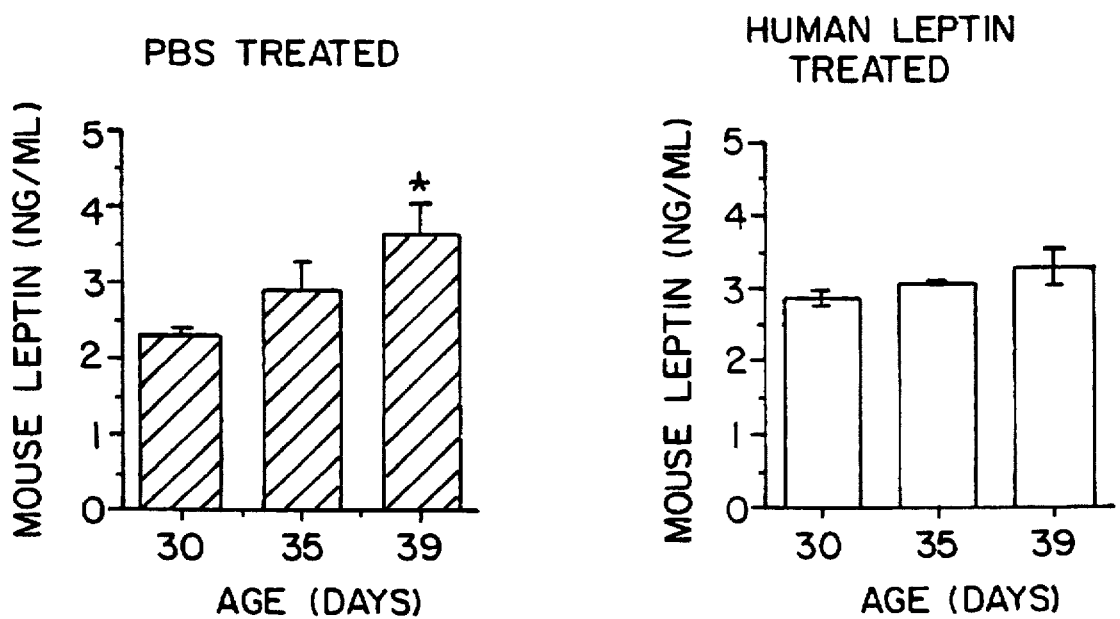

In order to determine the levels of endogenous leptin at the time of reproductive maturation, C57 BL/6J females were weaned at 24 days of age and treated with either PBS (n=12) or human recombinant leptin (n=12). Four animals from each group were sacrificed at 30, 35 and 39 days of age and blood collected for leptin measurements. The rationale of this experimental was two-fold: to assess endogenous leptin levels in vehicle treated mice at the time of reproductive maturation and to find out whether production of endogenous leptin is affected by the administration of exogenous leptin. As in the previous experiment, leptin treatment resulted consistently in a slowdown of body weight growth as shown in FIG. 9A. Plasma leptin levels in the vehicle group af 30, 35 and 39 days of age (FIG. 9B) consisted of 2.3±0.1 ng/ml, 2.9±0.4 ng/ml and 3.7±0.4 ng/ml. A 61% statistically significant increase (P=0.015) in leptin was thus found between 30 and 39 days of age. Interestingly, in the treated group, leptin levels did not rise but stabilized at 2.9–3.3 ng/ml showing that exogenous leptin treatment suppressed endogenous leptin production thereby suggesting the presence of a leptin producing feedback loop which usually increases endogenous leptin as the mouse progresses to puberty.

Overall, these findings demonstrated that leptin acts as a signal for puberty essentially as evidenced by its effects on the acceleration of reproduction in prepuberal mice, on vaginal opening, on the onset of the first estrous cycle and on maturation of reproductive tissues which are accompanied by changes in LH and 17-β-estradiol levels. The sites of actions of leptin could either be on the brain, on the ovaries or both since leptin receptors have also been identified on mouse ovaries (Chehab et al. *Nat. Gen.* 12:318–320 (1996)). However, the brain appears to be the prime target since transplantation of either the ob/ob or the db/db defective ovary into a normal mouse restores its function independent of whether the original host has a leptin (ob/ob) or leptin-receptor (db/db) defect.

III. Rescue of Male Sterility

A. Leptin treatment and food restriction of ob/ob males

Experiments were approved by the UCSF Committee on Animal Research. The animals were purchased from the Jackson Laboratories (Bar Harbor, Mee) and maintained each in individual cages at the UCSF Animal Care facility under a 12 hr. dark light regimen (lights on at 6 a.m., off at 6 p.m.). Human recombinant leptin was prepared as described above. Ten morbidly obese adult homozygous ob/ob males housed in individual cages were equally divided into a food-restricted group (ob/ob 1–5) and a leptin-treated group (ob/ob 6–10). In order to accelerate weight loss, the recombinant protein was injected daily intraperitoneally at a single dose of 20 μg/g initial body weight. The treatment was for 60 days to allow enough time for the food restricted ob/ob males to stabilize their body weight loss. Leptin-treated ob/ob males had continuous access to food whereas food-restricted ob/ob males were pair-fed to the leptin-treated group and allowed to consume daily 1 g of food (Purina-Mills, FormuLab Diet 5008) for 46 days and 3 g for the remaining 14 days. Water was provided without any restriction to both groups.

B. Matings of ob/ob mice

After 12 days of leptin treatment, 2 normal females were placed with each ob/ob male from both groups. Females with food-restricted ob/ob males were placed in the cage between 5 p.m. and 6 a.m. for mating after the ob/ob male had consumed the 1 g of food. These females were removed the next morning and placed collectively in cages where they access to food which they lacked of during the dark period. This cycle was repeated throughout the treatment.

C. Organ weights and histology

In order to determine some of the parameters that contributed to their fertility, control and leptin-treated ob/ob mice were sacrificed by an overdose of 2.5% Avertin at day 61 along with 5 lean male C57/BL mice and 3 untreated ob/ob males which were fed ad lib. To gain further insights into the effects of leptin treatment on the anatomy of the testis, histological examination of testicular sections from lean, untreated ob/ob, food restricted ob/ob and leptin treated ob/ob mice were carried out. The seminal vesicles and testis of all animals were weighed and histology of the testis examined. The seminal vesicles and testis were dissected and weighed immediately. The testis were then fixed in fresh 4% paraformaldehyde in PBS for 48 hours and processed for paraffin embedding, sectioning and hematoxylin and eosin staining. Statistics were determined by two-sample Student's t-test.

D. Food consumption and body weight of leptin-treated ob/ob males

Figure 10:
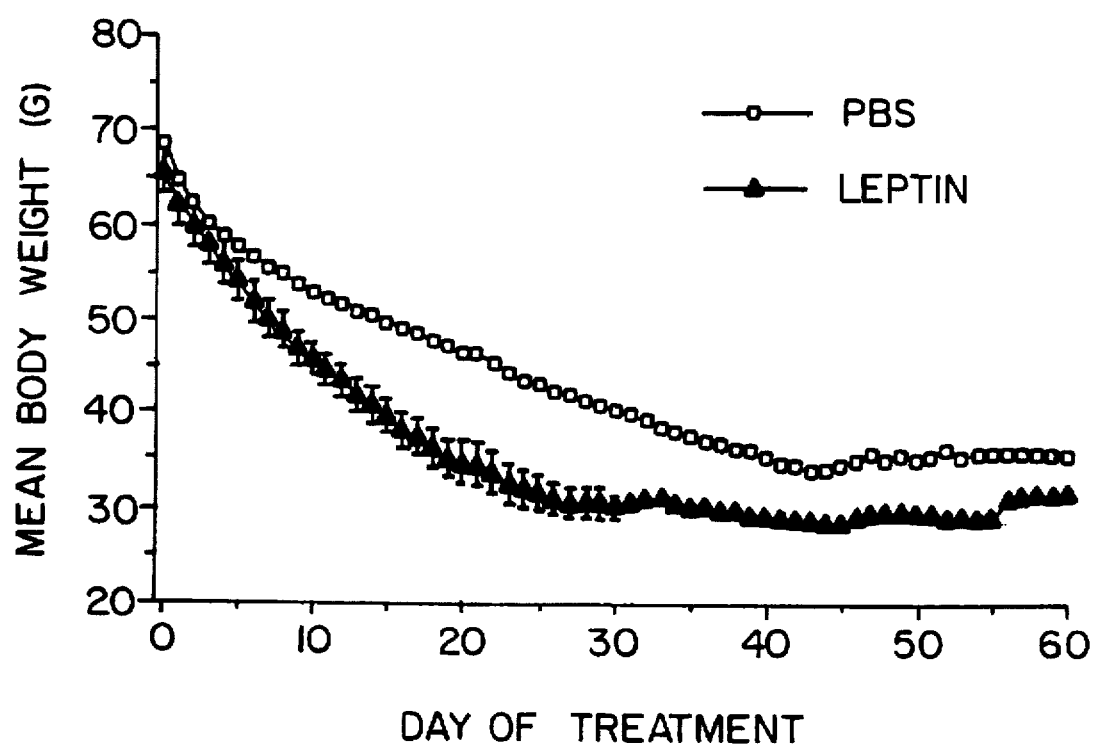
FIG. 10 depicts the effect of leptin treatment or food restriction on the body weights of ob/ob males. Body weights are expressed as means and s. e. m. of 5 animals per group. Standard errors for most points were too small to be shown on the plotted scale.

Mean daily food intake of each leptin treated ob/ob male during the first 12 days of treatment consisted of 0.8+0.1 g (Table 1). The food-restricted and leptin-treated groups entered the treatment, respectively, with 68.7+1.2 g and 65.6+2.2 g and lost respectively after 12 days of treatment 24.2+0.5% and 32.1+1.2% of their initial body weight (FIG. 10). Long term leptin treatment resulted in an increase of food consumption to approximately 2.9+0.3 g at day 45 (Table 1) which was used as a reference to increase the allotment of food to the food-restricted males for the last two weeks of treatment. The increase in food consumption of the leptin-treated ob/ob males could be as a result of partial resistance to the administered exogenous leptin. The body weights of 5 ob/ob mice treated for 12 days with a PBS vehicle solution did not significantly change (data not shown) and were thus excluded from subsequent matings since no weight loss was observed.

E. Fertility of ob/ob males

Each ob/ob mouse was housed at day 12 with 2 lean females to determine if weight loss, whether induced by food-restriction or leptin treatment, was accompanied with fertility. Demonstration of fertility in the leptin-treated ob/ob males was determined by the delivery of newborn pups 19–20 days after detection of the copulatory plug in lean females.

Food restriction of the ob/ob males resulted in a significant weight loss of 40.6±0.5% at 30 days and 48.1±1.8% at 60 days. However, none of the lean females that were mated with the food-restricted males had a copulatory plug nor any pregnancy resulted from diet-induced weight loss in the ob/ob males. Monitoring of body weight and food intake of the lean females revealed that they maintained a constant weight and consumed their food during the day since food was not available when they were placed with the food-restricted ob/ob males (data not shown). Therefore, induction of weight loss by food restriction in the ob/ob males did not result in correction of their sterility suggesting that excess adipose tissue is not the cause of sterility.

In contrast, mating of the 5 leptin-treated males with the 10 lean females resulted in copulatory plugs, pregnancies and deliveries in all the breeder females (Table II) demonstrating unequivocally successful functional reconstitution of the mate ob/ob reproductive system in the presence of leptin. Thus, correction of the sterility in ob/ob mice occurred despite an initial body weight of 65.6+2.2 g, thus indicating that accumulation of excessive fat does not permanently block the immaturity of the hypothalamic-pituitarygonadal axis which becomes functional as a result of leptin treatment.

F. Organ weights and testicular histology

Figure 11:
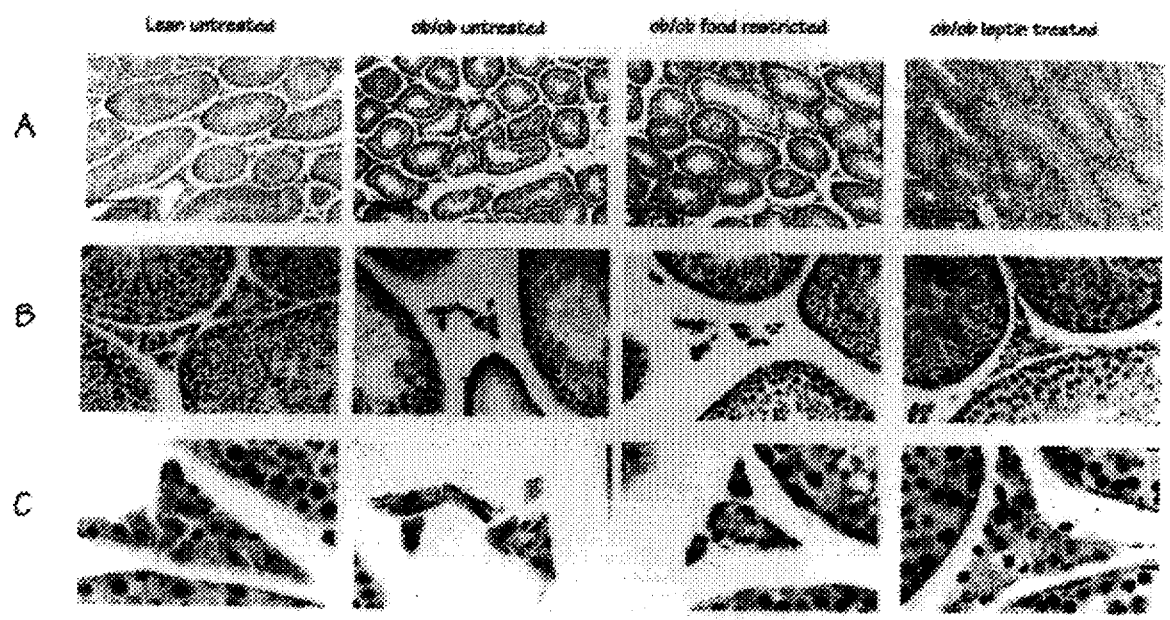
FIG. 11 depicts the hematoxylin and eosin stained sections of testis from lean, untreated ob/ob, food restricted ob/ob and leptin treated ob/ob mice. (A) Overall appearance of seminiferous tubules (100 ×magnification). The tubules are hollow and contain little sperm in the untreated and food-restricted ob/ob males. Lean and leptin-treated ob/ob males show normal tubules with abundant sperm. (B) (400×) Seminiferous tubules and Leydig cells. This view shows the sperm deficient lumen of the seminiferous tubules and shrunk interstitial Leydig cells in untreated and food-restricted ob/ob males. Leptin treated ob/ob males regained a testicular histology comparable to the 9 lean wild-type males. (C) (1000×) Magnification showing interstitial Leydig cells. The untreated and food-restricted ob/ob males show cytoplasm shrinkage of the Leydig cells, whereas the leptin-treated ob/ob males have normal Leydig cells identical to lean males.

Seminal vesicles weights were not statistically significant among the 4 groups. However, testis weight which is mostly indicative of overall spermatogenic activity and testosterone content was significantly different between lean and untreated ob/ob mice (P<0.001) and food-restricted versus leptin-treated ob/ob mice (P<0.001) as shown in Table III. Interestingly, comparison of the untreated ob/ob and food restricted ob/ob mice resulted in a 60% increase in testicular weight of the latter group (P<0.009) without, however, correction of their sterility. Thus, one effect of the leptin-induced fertility treatment is a normalization of testicular weight and function. Previous studies have shown that the overall structure of the ob/ob testis is abnormal and characterized most aberrantly by multinucleated spermatids, few spermatozoa and a small amount of interstitial Leydig tissue (STET) reduced by more than 50% (Hellman, B. Ann. N.Y. Acad. Sci. 131:541–558 (1965)). Consistent with these observations, two prominent histological features shown in FIG. 11 are noticeable. First, the lumen of the seminiferous tubules in the untreated and food restricted ob/ob males appear hollow and contain strikingly less sperm than the lean male mouse. Second, the interstitial Leydig cells of the obese mice are atrophied due visibly to a shrinkage in their cytoplasm. Food restriction of ob/ob males does not alter their abnormal histology and infertility as previously shown (Hellman et al. Acta Endocrinol. 44:20–26 (1963); Barash et al. Endocrinology 137:3144–3147 (1996)) and by the present experiments (FIG. 11).

In contrast, the seminiferous tubules of the leptin-treated ob/ob males become more abundant with mature sperms and the Leydig cells regain their usual morphology and clustering characteristic. Therefore, leptin treatment of the ob/ob males stimulates spermatogenesis and allows regeneration of the Leydig cells which should then be capable of producing adequate amounts of testosterone.

Therefore, the present study demonstrated that leptin treatment corrects the sterility of ob/ob males as effectively as in ob/ob females.

All references cited herein are incorporated by reference in their entirety for all purposes.

As will be understood by those of skill in the art, the present invention may be embodied in other specific forms without departing from the spirit and essential characteristics thereof. Accordingly, reference should be made to the appended claims for a description of the scope of the invention.

TABLE I

Daily food consumption (in grams) of the 5 leptin-treated ob/ob males during the first 12 days and at day 45 of the treatment.

| ob/ob | 6 | 7 | 8 | 9 | 10 |
|---|---|---|---|---|---|
| First 12 days | 0.9 ± 0.3 | 1.3 ± 0.3 | 0.5 ± 0.2 | 0.8 ± 0.2 | 0.6 ± 0.2 |
| Day 45 | 3.2 | 2.7 | 2.9 | 3.1 | 2.5 |

TABLE II

Litter sizes from lean females mated to ob/ob males in both groups.

| | Food restricted | | Leptin-treated | | |
|---|---|---|---|---|---|
| ob/ob mouse | pups born to female 1 | pups born to female 2 | ob/ob mouse | pups born to female 1 | pups born to female 2 |
| 1 | 0 | 0 | 6 | 4 | 3 |
| 2 | 0 | 0 | 7 | 9 | 3 |
| 3 | 0 | 0 | 8 | 5 | 8 |
| 4 | 0 | 0 | 9 | 6 | 9 |
| 5 | 0 | 0 | 10 | 5 | 5 |

TABLE III

Body, seminal vesicles and testis weights of lean C57/BL and ob/ob males either untreated, food-restricted or leptin-treated at the end of the treatment (day 61). Weights of the seminal vesicles and testis are expressed in mg per g body weight.

| | N | Body weight (g) | Sem. Vesicles (mg/g bw) | Testis (mg/g bw) |
|---|---|---|---|---|
| Lean C57/BL | 5 | 30.7 ± 1.3 | 13.8 ± 0.3 | 6.8 ± 0.3 |
| ob/ob untreated | 3 | 77.1 ± 1.8 | 10.5 ± 1.9 | 2.2 ± 0.2 |
| ob/ob food restricted | 5 | 36.8 ± 1.0 | 10.8 ± 0.6 | 3.5 ± 0.2 |
| ob/ob leptin treated | 5 | 31.7 ± 0.8 | 10.0 ± 0.8 | 6.4 ± 0.3 |

What is claimed is:

1. A method for restoring reproductive function in a reproductively impaired male or female host, wherein the host is reproductively impaired as a result of a hormonal deficiency, said method comprising administering a leptin compound to the host for a time and in an amount sufficient to restore or enhance reproductive function.

2. A method as in claim 1 wherein the leptin compound is administered to a female host from a time prior to impregnation through delivery of offspring.

3. A method as in claim 2, further comprising the administration of the leptin compound to a female host through lactation.

4. A method as in claim 1, wherein the leptin compound is a recombinant protein comprising the full length secreted form of leptin.

5. A method as in claim 1, wherein the leptin compound comprises at least a biologically active fragment of leptin.

6. A method as in claim 1, wherein the leptin compound comprises at least a biologically active fragment of leptin expressed as a fusion product in an expression vector.

7. A method as in claim 1, wherein the leptin compound is administered in a dosage from 0.1 ng/kg body weight to 100 mg/kg body weight.

8. A method as in claim 1, wherein the leptin compound is administered subcutaneously, intradermally, intravenously, intramuscularly, intraperitoneally, transdermally, orally, via pulmonary delivery, via intranasal delivery, via controlled release delivery, or via pump.

9. A method as in claim 1, wherein the leptin compound is administered continuously.

10. A method as in claim 1, wherein the leptin compound is administered in discrete doses.

11. A method as in claim 1, wherein the host suffers from a physiological defect of one or more hypothalamic, pituitary, or gonadal hormones.

12. A method as in claim 1, wherein the host is obese.

13. A method as in claim 1, wherein the host is non-obese.

14. A method as in claim 13, wherein the host has a body mass index of less than about 20.

15. A method of accelerating the onset of puberty in a male or female host, the method comprising administering a leptin compound to the host for a time and in an amount sufficient to cause the onset of puberty.

16. A method as in claim 15, wherein the leptin compound is a recombinant protein comprising the full length secreted form of leptin.

17. A method as in claim 15, wherein the leptin compound comprises at least a biologically active fragment of leptin.

18. A method as in claim 15, wherein the leptin compound comprises at least a biologically active fragment of leptin expressed as a fusion product in an expression vector.

19. A method as in claim 15, wherein the leptin compound is administered in a dosage from 0.1 ng/kg body weight to 100 mg/kg body weight.

20. A method as in claim 15, wherein the leptin compound is administered subcutaneously, intradermally, intravenously, intramuscularly, intraperitoneally, transdermally, orally, via pulmonary delivery, via intranasal delivery, via controlled release delivery, or via pump.

21. A method as in claim 15, wherein the leptin compound is administered continuously.

22. A method as in claim 15, wherein the leptin compound is administered in discrete doses.

23. A method as in claim 15, wherein the host suffers from a physiological defect of one or more hypothalamic, pituitary, or gonadal hormones.

24. A method as in claim 15, wherein the host is obese.

25. A method as in claim 15, wherein the host is non-obese.

26. A method as in claim 25, wherein the host has a body mass index of less than about 20.

* * * * *